(12) United States Patent
Pangan, Jr. et al.

(10) Patent No.: US 11,191,857 B2
(45) Date of Patent: Dec. 7, 2021

(54) MODULAR LIGHT ASSEMBLY FOR ULTRAVIOLET SANITIZING DEVICE

(71) Applicant: Vioguard Inc., Bothell, WA (US)

(72) Inventors: Roger R. Pangan, Jr., Kirkland, WA (US); Steven Michael Swedenburg, Wasilla, AK (US)

(73) Assignee: Vioguard Inc., Bothell, WA (US)

( * ) Notice: Subject to any disclaimer, the term of this patent is extended or adjusted under 35 U.S.C. 154(b) by 0 days.

(21) Appl. No.: 16/882,400

(22) Filed: May 22, 2020

(65) Prior Publication Data

US 2020/0282093 A1   Sep. 10, 2020

Related U.S. Application Data

(63) Continuation of application No. 16/556,888, filed on Aug. 30, 2019, now Pat. No. 10,682,432, which is a continuation of application No. 15/921,342, filed on Mar. 14, 2018, now Pat. No. 10,413,625.

(60) Provisional application No. 62/471,184, filed on Mar. 14, 2017.

(51) Int. Cl.

| A61L 2/10 | (2006.01) |
|---|---|
| G21K 5/02 | (2006.01) |
| A61L 2/24 | (2006.01) |
| G21K 5/08 | (2006.01) |
| G02B 5/08 | (2006.01) |
| A61L 2/26 | (2006.01) |
| G02B 1/00 | (2006.01) |

(52) U.S. Cl.
CPC ............ *A61L 2/10* (2013.01); *A61L 2/24* (2013.01); *A61L 2/26* (2013.01); *G02B 5/0891* (2013.01); *G21K 5/02* (2013.01); *G21K 5/08* (2013.01); *A61L 2202/121* (2013.01); *A61L 2202/122* (2013.01); *A61L 2202/14* (2013.01); *A61L 2209/12* (2013.01); *G02B 1/00* (2013.01)

(58) Field of Classification Search
CPC ..... A61L 2/10; A61L 2/24; A61L 2/26; A61L 2209/12; A61L 2202/121; A61L 2202/122; A61L 2202/14; G02B 5/0891; G02B 1/00; G21K 5/02; G21K 5/08
USPC .............. 250/455.11; 422/22, 23, 24, 186.3
See application file for complete search history.

(56) References Cited

U.S. PATENT DOCUMENTS

| 4,492,295 | A | * | 1/1985 | DeWoolfson | ......... G07F 7/0609 |
|---|---|---|---|---|---|
| | | | | | 100/902 |
| 4,757,205 | A | | 7/1988 | Latel et al. | |
| 5,019,256 | A | | 5/1991 | Ifill et al. | |
| 5,160,699 | A | | 11/1992 | Siegal | |

(Continued)

*Primary Examiner* — Kiet T Nguyen
(74) *Attorney, Agent, or Firm* — Seed Intellectual Property Law Group LLP

(57) ABSTRACT

A modular light assembly for an ultraviolet (UV) treatment device includes a UV light reflective surface. First and second sidewalls are coupled to respective sides of the reflective surface. Electrical input contacts are formed on each of the first and second sidewalls for receiving electrical power, and electrical output contacts are formed on each of the first and second sidewalls for delivering electrical power. A plurality of UV lamps are included, each of which have a first end and a second end. The first end of each of the UV lamps is coupled to a respective one of the electrical output contacts on the first sidewall, and the second end is coupled to a respective one of the electrical output contacts on the second sidewall.

10 Claims, 3 Drawing Sheets

(56) References Cited

U.S. PATENT DOCUMENTS

| | | |
|---|---|---|
| 7,888,657 B1 | 2/2011 | Zadro |
| 8,765,072 B2 | 7/2014 | Morneault |
| 9,254,342 B2 | 2/2016 | Engelhardt et al. |
| 9,364,573 B2 | 6/2016 | Deshays et al. |
| 2009/0218512 A1 | 9/2009 | Ranta et al. |
| 2010/0044582 A1 | 2/2010 | Cooper et al. |
| 2010/0266445 A1 | 10/2010 | Campagna |

\* cited by examiner

MODULAR LIGHT ASSEMBLY FOR ULTRAVIOLET SANITIZING DEVICE

BACKGROUND

Technical Field

The present disclosure generally relates to ultraviolet (UV) sanitizing devices, and more particular, to UV sanitizing devices having a modular light assembly that plugs into a main circuit board in an interior of the device.

Description of the Related Art

It is well known that ultraviolet light has germicidal properties, and can be utilized for sanitizing or disinfecting of surfaces. Various UV treatment devices are known for sanitizing, for example, devices such as keyboards which may be shared by multiple users and thus may facilitate the transfer of germs between users.

UV treatment devices are generally sophisticated and, in some respects, dangerous to untrained users. Accordingly, such devices are typically maintained only be professional service providers, or by the manufacturer of the devices. This can limit the utility of such UV treatment devices to many users, since repairs such as replacing UV lamps may require an appointment with a service technician, or the like.

Additionally, known UV treatment devices generally have very specific and limited uses. For example, a UV treatment device may be limited to use with a particular keyboard, which may further limit the utility of such UV treatment devices to many end-users.

All of the subject matter discussed in the Background section is not necessarily prior art and should not be assumed to be prior art merely as a result of its discussion in the Background section. Along these lines, any recognition of problems in the prior art discussed in the Background section or associated with such subject matter should not be treated as prior art unless expressly stated to be prior art. Instead, the discussion of any subject matter in the Background section should be treated as part of the inventor's approach to the particular problem, which in and of itself may also be inventive.

BRIEF SUMMARY

The present disclosure provides systems, devices and methods for sanitizing user computer devices, such as a keyboard, mouse, mobile phones or the like, utilizing UV light.

In one embodiment, the present disclosure provides a modular light assembly for a UV treatment device that includes a UV light reflective surface; first and second sidewalls coupled to respective sides of the reflective surface, the first and second sidewalls each including electrical input contacts for receiving electrical power, and output contacts for delivering electrical power; and a plurality of UV lamps, each of the UV lamps coupled between respective output contacts of the first and second sidewalls.

In another embodiment, the present disclosure provides a UV treatment device that includes a housing having an interior that at least partially defines a UV treatment chamber. The housing includes a door that provides access to the interior. A main circuit board is positioned along a rear portion of the interior of the housing, and the main circuit board includes electrical receptacles for supplying electrical power. The UV treatment device further includes a light assembly that includes: a UV light reflective surface; first and second sidewalls coupled to respective sides of the reflective surface, the first and second sidewalls each including electrical input contacts that are releasably coupled to respective receptacles of the main circuit board, and output contacts for delivering electrical power; and a plurality of UV lamps, each of the UV lamps coupled between respective output contacts of the first and second sidewalls.

BRIEF DESCRIPTION OF THE SEVERAL VIEWS OF THE DRAWINGS

Non-limiting and non-exhaustive embodiments are described with reference to the following drawings, wherein like labels refer to like parts throughout the various views unless otherwise specified. The sizes and relative positions of elements in the drawings are not necessarily drawn to scale. For example, the shapes of various elements are selected, enlarged, and positioned to improve drawing legibility. The particular shapes of the elements as drawn have been selected for ease of recognition in the drawings. One or more embodiments are described hereinafter with reference to the accompanying drawings in which.

DETAILED DESCRIPTION

The present disclosure generally provides systems, devices and methods for sanitizing user computer devices and/or peripheral devices, such as a keyboard, mouse, mobile phones or the like, utilizing UV light. In one or more embodiments, the disclosure provides a modular light tray, for use in a UV treatment system, which is conveniently and easily replaceable by an end-user. Additionally, the disclosure provides a UV treatment drawer or tray that can be ejected from an inner chamber of a UV treatment device, and that includes compartments sized for holding various user devices during UV treatment.

While the term "UV" light is generally used throughout the present disclosure, that term is used herein to more specifically refer to UV light which is effective for germicidal treatment. In particular, "UV" light as used herein, refers to short-wave, germicidal UV light, which is also known as ultraviolet C or "UVC" light.

Figure 1:
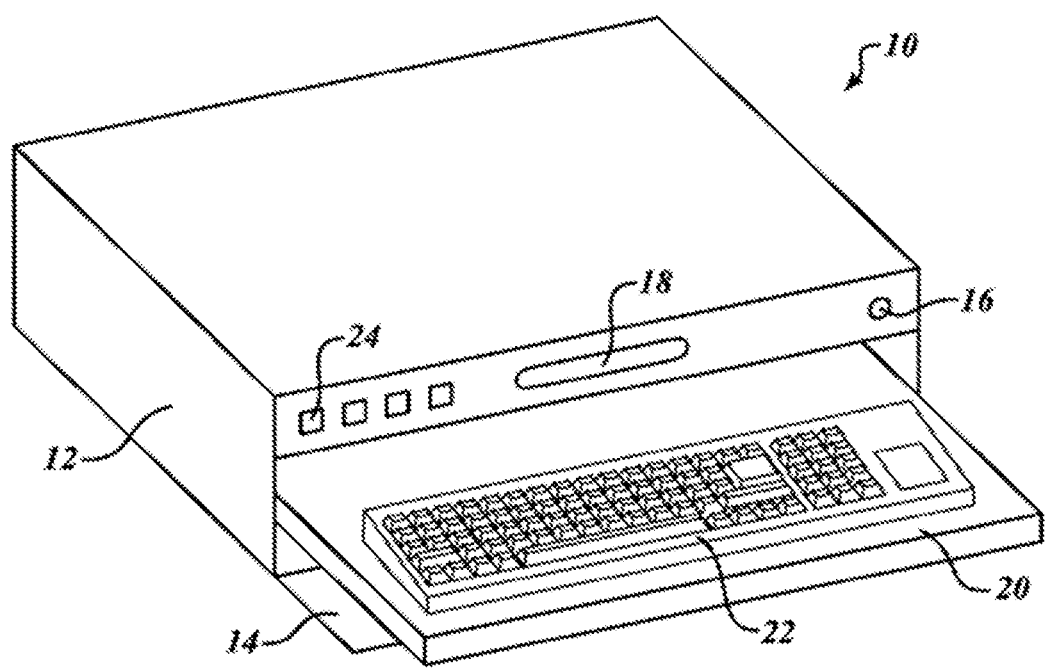
FIG. 1 is a diagram illustrating a UV treatment device, in accordance with one or more embodiments of the present disclosure.

FIG. 1 is a diagram illustrating a UV treatment device 10, in accordance with one or more embodiments of the present disclosure. The device 10 includes a housing 12 having a door 14 located on a front surface of the housing 12. With the door 14 closed, an interior of the housing 12 generally defines a UV treatment chamber for treating or sanitizing devices (such as a keyboard, or other user input or computer devices).

The door 14 may be manually operated, or may be automatically operated. For example, the device 10 may include a manually-operated button 16, such as a spring-loaded button, that is coupled to a locking mechanism for the door 14. When a user presses the button 16, the door 14 may thus be automatically, and mechanically, opened. Additionally or alternatively, the device 10 may include a touchless sensor 18 that allows a user to open and/or close the door 14 by waving a hand in front of the sensor 18.

When the door 14 is opened, a sliding drawer 20 is ejected from within the housing 12. The sliding drawer 20 holds and conveys one or more items to be sanitized (e.g., a keyboard 22) between an extended position (i.e., at least partially extended outside of the housing 12) and a retracted position (i.e., contained within the housing 12).

The drawer 20 may be driven by a motor between the extended and retracted positions. For example, when the door 14 is opened, the motor may automatically drive the drawer 20 into the extended position for using the keyboard 22, or for loading other items to be sanitized onto the drawer 20. Similarly, the drawer 20 may be retracted into an interior portion of the housing 12 by the motor, and the door 14 may then be closed (e.g., utilizing the touchless sensor 18), and the UV treatment device 10 can begin a UV treatment cycle.

Alternatively, the drawer 20 may be ejected by a spring-loaded or other mechanical mechanism that automatically ejects the drawer 20 into the extended position upon, for example, pressing the button 16.

The drawer 20 may include a generally flat shelf, and may be secured to the interior of the housing 12 via sliding rails, telescoping extensions, or the like. In one embodiment, the drawer 20 includes telescoping extensions attached to a lower surface of the drawer 20 and the telescoping extensions are operable to extend the drawer 20 outside of the housing 12, and retract the drawer 20 back inside of the housing.

In one embodiment, a keyboard 22 is provided on the drawer 20, and in some configurations the lower surface of the keyboard 22 may serve as the drawer 20 (i.e., the keyboard 22 may be included as part of the UV treatment device 10, and is not detachable therefrom). Alternatively, in one or more other embodiments, a keyboard is not included as part of the device 10, and the drawer 20 includes one or more compartments for holding various user computer devices and/or peripheral devices for UV treatment within the device 10. For example, the drawer 20 may include compartments sized for holding a mobile phone, a user's keyboard that is separable from the device 10, or any other device. In such a case, a user may place one or more devices into the appropriate compartment of the drawer 20, and the drawer 20 may be retracted into the housing 12 for UV sanitation.

The UV treatment device 10 may include various components, features and functionalities that are described, for example, in U.S. Pat. No. 8,084,752, which is assigned to the assignee of the present application, and the entire contents of which is incorporated by reference herein.

The UV treatment device 10 may include a microcontroller 92, a motor driver and a motor, housed within the housing 12, that drive the drawer 20 the appropriate direction and speed when opening and closing the door 14 and moving the drawer 20 between the retracted and extended positions.

The motor may be a DC motor, and the drawer 20 may be manually operated without damaging the motor, and any stopping or slowing of the drawer mechanism during activation can be sensed by the microcontroller 92 and will result in stopping or reversing the drawer mechanism so as to not pinch hands or objects in the drawer 20.

The device 10 may further include a safety interlock circuit 94 (which may be housed within the housing 12) that will interrupt power to the UV lamps in the event that the drawer 20 is manually forced open during a UV sanitization cycle. The safety interlock circuit 94 may include one or more optical 96 or mechanical switches 98 which indicate to the microcontroller 92 that the door 14 is fully closed. In addition, the safety interlock circuit 94 supplies power to a lamp driver (which provides power to the UV lamps) only when the door is fully closed, providing protection against failure of the microcontroller 92.

A power supply 90 is included in the device 10 and converts AC power or external DC power to voltages utilized by internal circuitry within the housing 12. A USB controller may be included that facilitates communication between a host PC and the keyboard 22. The microcontroller 92 may monitor input activity via the keyboard 22, and can initiate a UV treatment sterilization cycle after a period of inactivity (which may be user selectable).

The UV treatment cycle may be initiated in a variety of ways. In one embodiment, the UV treatment cycle is triggered by a treatment button that may be provided on the keyboard 22, on the sliding drawer 20, or at another location on an exterior of the housing 12. In the case of a button on the housing 12 (e.g., the button 16, the touchless sensor 18 or another button on an exterior of the housing 12) or drawer 20, the button may be connected to a microcontroller 92 (which may be housed within the housing 12) that initiates the UV treatment cycle.

As noted previously herein, in one or more embodiments, the device 10 may include a touchless sensor 18 (such as an infrared proximity sensor, or the like) mounted on the device 10 at any location, including for example on an exterior of the housing 12, on the drawer 20, or on the keyboard 22. A user may thus wave a hand near the touchless sensor 18 to retract the drawer 20 and begin a UV treatment cycle.

The touchless sensor 18 is in communication with a microprocessor and memory having stored programming instructions (or logic). Upon sensing a hand or other object within a particular distance to the sensor 18, the drawer 20 will retract within the housing 12, the door 14 will close, and a UV treatment cycle will begin.

Figure 2:
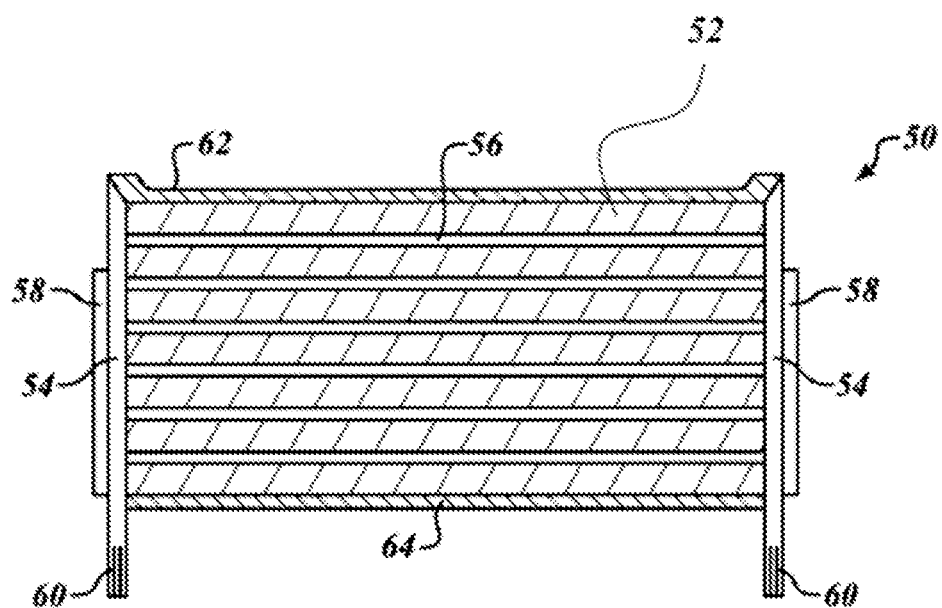
FIG. 2 is a diagram illustrating a modular light assembly that can be inserted into, and removed from, the UV treatment device of FIG. 1, in accordance with one or more embodiments.

With the drawer 20 retracted within the housing 12, and the door 14 being in the closed position, a light tight UV treatment chamber is formed within an interior of the housing 12. Once the door 14 is closed, the microprocessor causes illumination of one or more germicidal UV lamps, which are shown in FIG. 2, and which are positioned near a ceiling of the interior of the housing 12. During the UV treatment cycle, one or more status indicators 24 may be illuminated to indicate that a cycle is in process, or to indicate various conditions associated with the UV treatment device 10. A UV treatment cycle may take anywhere from a few seconds to several minutes or more, depending on input settings that may be provided by a user. In one embodiment, a standard default cycle length is programmed into or otherwise provided by the control logic, with the default cycle length being set to correspond to a dosage of UVC light that is sufficient to sanitize germs most likely to be present on the keyboard 22 or other devices which may be positioned on the drawer 20 (e.g., within an appropriate compartment which may be formed in the drawer 20) for UV treatment.

The dosage is preferably measured in terms of actual UV light emitted within the UV treatment chamber formed inside of the housing 12. When the UV treatment cycle is complete, status indicators 24 will indicate the sanitization is complete and the drawer 20 will remain retracted within the housing 12 until a user causes the drawer 20 to be ejected, for example, by pressing the button 16 or by actuating the touchless sensor 18.

The dosage of the UV light may be measured by an optical sensor 96 or dosimeter that is positioned within the interior of the housing 12 and is coupled to the microcontroller 92. When a desired UV dosage has been reached, the microcontroller 92 can cause the UV lamps to shut off.

Dosage ranges for the UV treatment cycles may be stored in a memory accessible by the microprocessor in order to ensure that the keyboard 22 or other device to be treated has been properly disinfected. In one or more embodiments, the memory stores information indicating UV dosages for disinfecting or killing particular pathogens. A user may thus control the UV treatment device 10, e.g., through a connection to a personal computer, and the user may select a particular UV dosage level for a UV treatment cycle that corresponds to particular types of pathogens.

Figure 3:
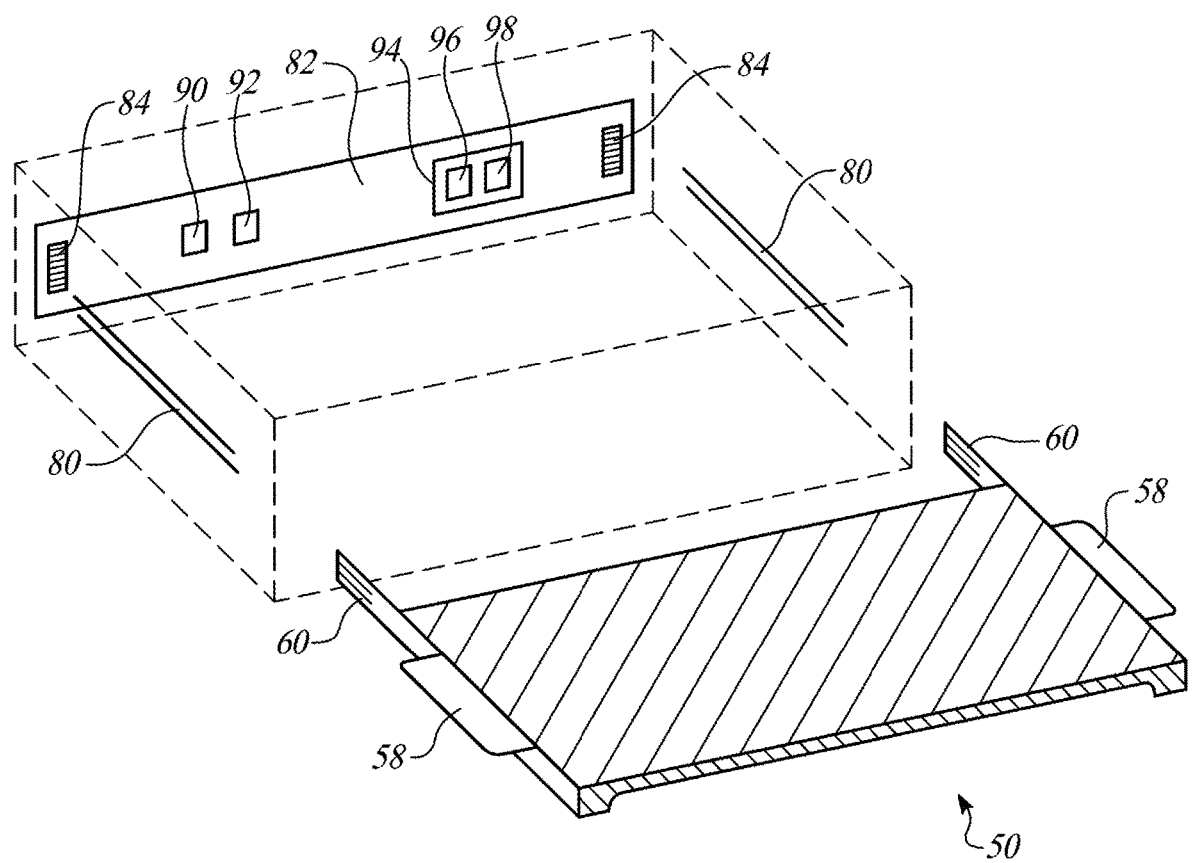
FIG. 3 illustrates insertion of the modular light assembly into an interior portion of the UV treatment device, in accordance with one or more embodiments.

FIG. 2 illustrates a modular light assembly 50 that can be easily inserted into, and removed from, the UV treatment device 10 of FIG. 1. FIG. 3 illustrates an interior portion of the UV treatment device 10 and shows how the modular light assembly 50 is inserted into the interior of the housing 12 of the device 10. The light assembly 50 is shown in an upside-down view in FIG. 2, in order to better illustrate the features of the light assembly 50. That is, when the light assembly 50 is inserted into the UV treatment device 10, as shown in FIG. 3, it is flipped over with respect to the view of FIG. 2.

The light assembly 50 includes a UV reflecting surface 52, sidewalls 54 and a plurality of UV lamps 56 extending between the sidewalls 54. The light assembly 50 further includes two or more extensions 58 that protrude outwardly beyond outer side surfaces of each of the sidewalls 54.

As shown in FIG. 3, the extensions 58 of the light assembly 50 fit into guide rails 80 that are positioned on inner side surfaces of the UV treatment device 10, e.g., on inner side surfaces of the housing 12. To insert the light assembly 50 into the UV treatment device 10, a user can simply insert the light assembly 50 into an upper interior portion of the housing 12 until the extensions 58 are received inside of the guide rails 80. Once received by the guide rails 80, the light assembly 50 is guided into the proper position within the UV treatment device 10 as the user pushes the light assembly 50 fully into the UV treatment device 10.

At least a portion of the sidewalls 54 of the light assembly 50 includes conductive paths for providing electricity to the UV lamps 56. In one or more embodiments, each of the sidewalls 54 is formed of, or at least partially includes, a respective circuit board for providing electrical power supplied from a main circuit board 82 positioned within the housing 12 (e.g., along a back wall inside of the housing 12) of the UV treatment device 10 to the UV lamps 56. In such a case, the sidewall circuit boards may include various circuitry (including, for example, resistors, diodes, microprocessors, ballasts, etc.) for conditioning, filtering or otherwise processing the input electrical power and for delivering electrical power suitable for powering the UV lamps 56.

In that regard, the sidewalls 54 of the light assembly 50 may include electrical contacts 60 formed on rear surfaces (i.e., the leading edge or surface that is inserted into the housing 12) of the sidewalls 54. The contacts 60 may be formed within an electrical plug or tab connected to the sidewalls 54, or they may be exposed contacts (as shown) formed on the sidewalls 54.

The main circuit board 82 includes receptacles 84, and the contacts 60 of the light assembly 50 can be plugged into the receptacles 84 of the main circuit board 84. By sliding the light assembly 50 into the UV treatment device 10 (e.g., with the extensions 58 being guided by the guide rails 80), the contacts 60 of the sidewalls 54 of the light assembly 50 are guided into the receptacles 84 of the main circuit board 84. At this point, an electrical path is established between the main circuit board 84, the sidewalls 54 (e.g., the circuit boards on the sidewalls 54) and the UV lamps 56.

The light assembly 50 may remain plugged into the receptacles 84 of the main circuit board 84 within the housing 12 until such time as one or more of the UV lamps 56 burns out or otherwise becomes inoperable. At such time, the UV lamps 56 can be easily replaced by removing the light assembly 50 (e.g., by opening the door 14 and then sliding the light assembly 50 out of the housing 12), and then inserting a new light assembly 50 with new UV lamps 56.

In one or more alternative embodiments, the light assembly 50 may include sockets or receptacles into which the UV lamps 56 can be inserted and removed. In such a case, the entire light assembly 50 does not need to be replaced when one or more UV lamps 56 becomes inoperable, but instead, the light assembly 50 may be pulled out of the housing 12, the defective UV lamps 56 may be replaced, and the light assembly 50 may be pushed back into its proper position within the housing 12.

The modular design of the light assembly 50 provides significant advantages over UV treatment devices having relatively inaccessible UV lamps housed within the device. Typically, a trained service professional is needed to change the UV lamps of such devices, since removal and replacement of the lamps may require substantial disassembly of the device itself. Removal and replacement of lamps in such devices thus may require an in-person visit by such a professional, or may otherwise require that the entire device be sent to the manufacturer for replacement of the UV lamps. The modular light assembly 50 provided by the present disclosure, on the other hand, is easily removable and replaceable by the end-user and can be performed without any tools and without disassembly the housing 12 or any other portion of the UV treatment device 10.

The reflective surface 52 of the light assembly 50 may be made of any material that reflects UV light. In one embodiment, the reflective surface 52 is made of unpolished aluminum, which the inventors have found to desirably reflect UV light, and further, to desirably scatter the reflected UV light at various angles, as may be desirable in order to provide UV light throughout the UV light chamber.

The reflective surface 52 may be a substantially flat surface in one or more embodiments. In alternative embodiments, the reflective surface 52 may have various surface profiles or geometries in order to scatter UV light that is incident upon the reflective surface 52. For example, in one or more embodiments, the reflective surface 52 may have a rough profile, a wavy profile, a sharp or angular profile, or any other surface profile as may be desired for scattering or providing diffuse reflection of UV light incident upon the reflective surface 52.

Additionally, in one or more embodiments, the light assembly 50 may include a front wall 62 and a back wall 64, each of which extends downward from the reflective surface 52 (which forms a ceiling of the UV chamber within the housing 12, when the light assembly 50 is inserted in the UV treatment device 10). The front and back walls 62, 64 may be UV reflective and may be made of the same material as the reflective surface 52 (e.g., unpolished aluminum). Additionally, the sidewalls 54 (which may be or include respective sidewall circuit boards) may be coated or otherwise treated with a reflective material so that the sidewalls 54 operably reflect UV radiation emitted by the UV lamps 56.

Figure 4:
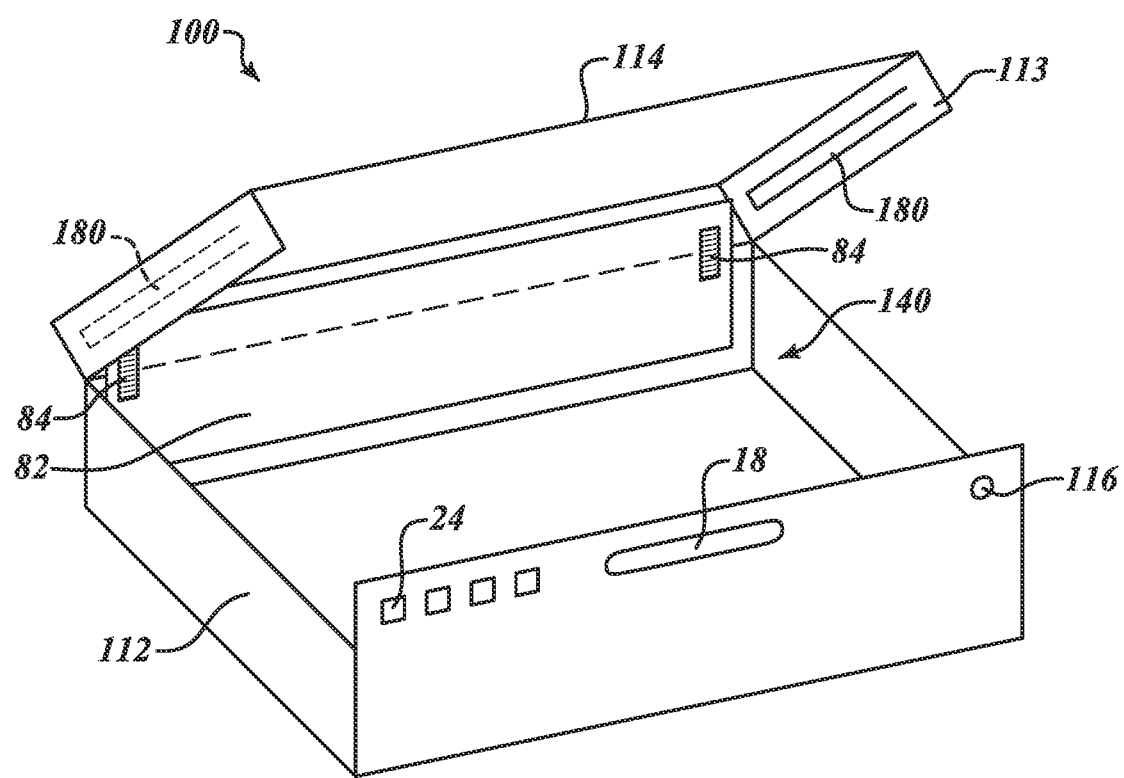
FIG. 4 is a diagram illustrating another UV treatment device, in accordance with one or more embodiments of the present disclosure.

FIG. 4 is a diagram illustrating a UV treatment device 100, in accordance with one or more embodiments of the present disclosure. The UV treatment device 100 is similar to the UV treatment device 10 shown in FIG. 1, except that the device 100 is a top-loading treatment device. That is, instead of having a door 14 on a front surface of the housing 12, the UV treatment device 100 includes a rotatable door 114 that forms an upper portion of the housing 112. The door 114 includes an upper or top surface of the housing 112 and further includes upper sidewall portions 113 of the housing 112. One or more hinges may be provided, e.g., along a back surface of the housing 112, and the hinges may thus rotatably couple the door 114 to the base portion of the housing 112.

The door 114 may be selectively operable in open (as shown in FIG. 3) and closed positions. In the closed position, i.e., with the door 114 rotated downward toward the front surface of the housing 112, an interior of the housing 112 generally defines a UV treatment chamber for treating or sanitizing devices, such as a keyboard, mobile phone, other user input or computer devices, pen, or any other object to be sanitized.

The door 114 may be manually operated, or may be automatically operated. For example, the device 100 may include a manually-operated button 116, such as a spring-loaded button, that is coupled to a locking mechanism for the door 114. Moreover, the door 114 may be biased toward the open position by a biasing element such as one or more springs or the like. However, in the closed position, a locking mechanism may hold the door 114 closed even though the biasing element applies a biasing force toward the open position. When a user presses the button 116, the door 114 may thus be automatically, and mechanically, opened as the locking mechanism is unlocked and the biasing element pushes the door 114 into the open position. Additionally or alternatively, the device 100 may include a touchless sensor 18 for opening the door 114, and the touchless sensor 18 may be the same as described above with respect to the UV treatment device 10 shown in FIG. 1.

When the door 114 is opened, the treatment chamber 140 is accessible to the user, and the user may place one or more devices into the treatment chamber 140 for UV sanitization. That is, the user may place the devices into the treatment chamber 140 and then close the door 114 and initiate a UV sanitization cycle in the same manner as described above with respect to the UV treatment device 100 shown in FIG. 1.

Moreover, with the door 114 in the open position, the modular light assembly 50 (shown in FIG. 2) is accessible, and the light assembly 50 can be easily removed by a user, for example, to inspect or replace the UV lamps 56. Although not shown in FIG. 4, the modular light assembly 50 included in the UV treatment device 100 may be the same, or substantially the same, as the modular light assembly 50 shown in FIG. 2.

The door 114 includes guide rails 180 that are positioned on inner side surfaces of the door 114. The guide rails 180 may be substantially the same as the guide rails 80 shown in FIG. 3. The guide rails 180 may be open toward a front surface so that the guide rails 180 can receive the extensions 58 of the light assembly 50 and guide the light assembly 50 into a desired position as the light assembly 50 is pushed toward the back surface of the housing 112. Moreover, in some embodiments, the guide rails 180 may have end surfaces located toward the back surface of the housing 112 which prevent the light assembly 50 from moving any further toward the back of the housing 112. The end surfaces of the guide rails 180 may thus be positioned so that when the light assembly 50 is inserted into the guide rails 180 and in abutting contact with the end surfaces of the guide rails 180, the electrical contacts 60 of the light assembly 50 will be properly aligned with and mated to the receptacles 84 on the main circuit board 82 when the door 114 is rotated downward to the closed position. For example, in one or more embodiments, the guide rails 180 may be positioned to hold the light assembly 50 in such a way that upper edges of the electrical contacts 60 are touching or nearly touching corresponding upper edges of the receptacles 84 with the door 114 in the open position. When the door 114 is rotated downward to the closed position, the lower edges of the electrical contacts 60 are rotated toward the back surface of the housing 112 and are guided by the rotation of the door 114 into the receptacles 84 for proper electrical connection.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheetare incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. An ultraviolet (UV) treatment device, comprising:
a housing;
a UV treatment chamber within the housing;
a door coupled to the housing that provides access to the UV treatment chamber;
a UV light assembly that includes a plurality of UV light sources, the UV light assembly further including two or more extensions that protrude outwardly towards sidewalls of the housing;
a power supply positioned within the housing, the power supply selectively providing power to cause each of the plurality of UV light sources to emit UV light;
a safety circuit configured to prevent power from being provided to the UV light sources by the power supply, the safety circuit including both an optical sensor switch and a door fully closed switch to prevent power from going to the UV light sources if either switch indicates that the door is open, and
guide rails on inner side surfaces of the housing that are positioned to receive the extensions of the UV light assembly into the inner side surfaces of the UV treatment device.

2. The UV treatment device of claim 1, wherein the door fully closed switch is a mechanical switch.

3. The UV treatment device of claim 1 wherein the safety circuit is positioned within the housing.

4. The UV treatment device of claim 1, further comprising:
  a microcontroller positioned in the housing, the microcontroller receiving input from both the optical switch and the door fully closed switch and interrupting power to the UV lights if either of the two switches indicates that the door is open.

5. An ultraviolet (UV) treatment device, comprising:
  a housing;
  a UV treatment chamber within the housing, the UV treatment chamber including one or more reflective surfaces with a surface profile that scatters UV light that is incident upon the reflective surface;
  a door coupled to the housing that provides access to the UV treatment chamber;
  a UV light assembly that includes a plurality of UV light sources;
  a power supply positioned within the housing, the power supply selectively providing power to cause each of the plurality of UV light sources to emit UV light;
  a safety circuit configured to prevent power from being provided to the UV light sources by the power supply, the safety circuit including both an optical sensor switch and a door fully closed switch to prevent power from going to the UV light sources if either switch indicates that the door is open.

6. The ultraviolet (UV) treatment device of claim 5, wherein the surface profile of the one or more reflective surfaces is a rough profile.

7. The ultraviolet (UV) treatment device of claim 5, wherein the surface profile of the one or more reflective surfaces is a wavy profile.

8. The ultraviolet (UV) treatment device of claim 5, wherein the surface profile of the one or more reflective surfaces is a sharp profile.

9. The ultraviolet (UV) treatment device of claim 5, wherein the surface profile of the one or more reflective surfaces is an angular profile.

10. The ultraviolet (UV) treatment device of claim 5, wherein the surface profile of the one or more reflective surfaces provides diffuse reflection of UV light incident upon the reflective surface.

\* \* \* \* \*